(12) United States Patent
Nemoto et al.

(10) Patent No.: US 6,650,929 B1
(45) Date of Patent: Nov. 18, 2003

(54) CONTRAST MEDIA INJECTION APPARATUS

(75) Inventors: Shigeru Nemoto, Tokyo (JP); Kazuaki Mizoguchi, Okayama (JP); Taro Saito, Kumamoto (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 28 days.

(21) Appl. No.: 09/680,016

(22) Filed: Oct. 5, 2000

(30) Foreign Application Priority Data

Oct. 5, 1999 (JP) .......................................... 11-284220

(51) Int. Cl.$^7$ ................................................ A61B 6/00
(52) U.S. Cl. ........................ 600/431; 604/30; 604/246
(58) Field of Search .......................... 604/250, 9, 513, 604/99.02, 99.03, 118, 119, 121, 124, 125, 167.06, 173, 236, 539, 284, 288.03, 30, 246; 600/431–435

(56) References Cited

U.S. PATENT DOCUMENTS

| | | | |
|---|---|---|---|
| 3,834,372 A | * 9/1974 | Turney | 600/561 |
| 4,030,498 A | 6/1977 | Tompkins | |
| 4,219,021 A | * 8/1980 | Fink | 137/556.6 |
| 4,253,501 A | 3/1981 | Ogle | |
| 4,432,392 A | 2/1984 | Paley | |
| 5,104,387 A | * 4/1992 | Pokorney et al. | 604/248 |
| 5,106,363 A | * 4/1992 | Nobuyoshi | 604/4 |
| 5,127,904 A | 7/1992 | Loo et al. | |
| 5,232,024 A | 8/1993 | Williams | |
| 5,356,375 A | * 10/1994 | Higley | 604/142 |
| 5,423,751 A | * 6/1995 | Harrison et al. | 604/83 |
| 5,569,208 A | * 10/1996 | Woelpper et al. | 604/183 |
| 5,573,515 A | * 11/1996 | Wilson et al. | 604/236 |
| 5,593,385 A | * 1/1997 | Harrison et al. | 604/83 |
| 5,800,397 A | * 9/1998 | Wilson et al. | 137/625.67 |
| 6,099,502 A | * 8/2000 | Duchon et al. | 128/DIG. 12 |
| 6,099,511 A | * 8/2000 | Devos et al. | 604/246 |
| 6,371,942 B1 | * 4/2002 | Schwartz et al. | 137/606 |

FOREIGN PATENT DOCUMENTS

| | | |
|---|---|---|
| GB | 2274 148 A | 7/1994 |
| WO | WO 99/21481 | 5/1999 |

* cited by examiner

Primary Examiner—Brian L. Casler
Assistant Examiner—Kevin C. Sirmons
(74) Attorney, Agent, or Firm—Knobbe Martens Olson & Bear, LLP

(57) ABSTRACT

A contrast media injection apparatus has (a) a manifold having a port for connection of catheter, a port for connection of contrast media line, a port for connection of pressure-monitoring line and a port for connection of physiological saline solution line, (b) a pressure-monitoring line connected to the port for connection of pressure-monitoring line and having a cutoff mechanism in the middle, (c) a contrast media line connected to the port for connection of contrast media line, and (d) a contrast media injector connected to the back end of the contrast media line. Using the injection apparatus, the monitoring of pulsation and the injection of contrast media can be conducted under no radiation exposure and, moreover, the injection of contrast media can be conducted simply without requiring the complex operation of valve switching.

13 Claims, 6 Drawing Sheets

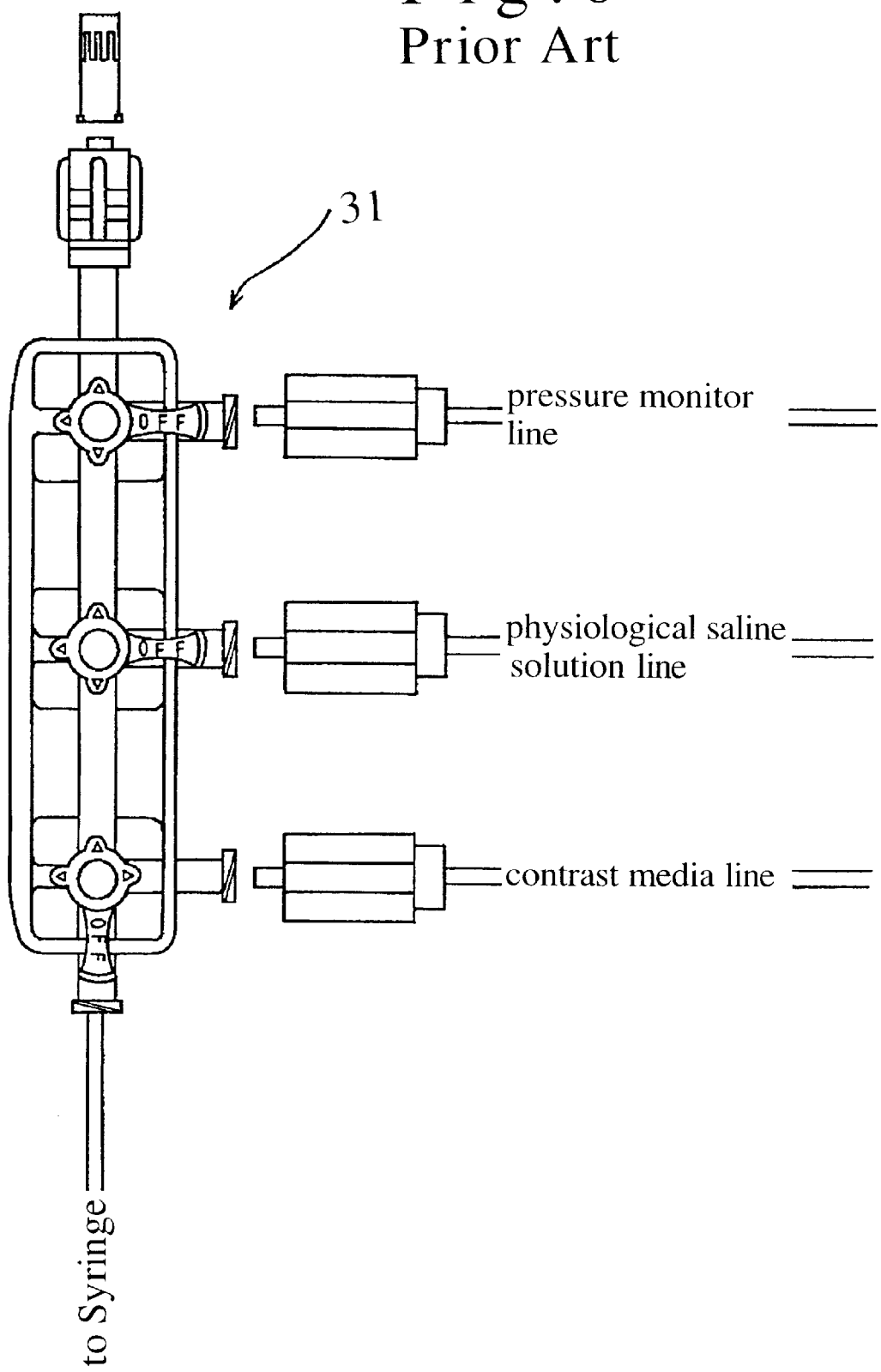

CONTRAST MEDIA INJECTION APPARATUS

BACKGROUND OF THE INVENTION

1. Field of the Invention

The present invention relates to a contrast media injection apparatus used in angiography or the like.

2. Description of the Prior Art

In recent years in the field of treatment of circulatory system diseases, radiography has come to be widely used for treatment under fluoroscopy as well as for simple diagnosis. The treatment under fluoroscopy includes, for example, (1) a treatment which comprises inserting a catheter into a patient with the disease part of the patient being confirmed by radiography, and injecting a thrombolytic substance to the thrombus-occluded site of vessel to reopen the vessel site and (2) a treatment which comprises inserting a catheter having a balloon at the front end, to the stricture site of vessel and allowing the balloon to expand to widen the stricture site.

In a treatment in which the thrombus generated in coronary artery is dissolved, a catheter is inserted as deep as the occluded site of coronary artery and a thrombolytic agent is spouted from the front end of the catheter, as shown in, for example, FIG. 5. Even under fluoroscopy, an image of a target vessel is not obtained when no contrast media is used; therefore, a contrast media is used for confirmation of occluded vessel site or for insertion of catheter to coronary artery. Further, for safety of the patient, insertion of catheter is conducted while checking the blood pressure of patient.

A manually operated triple three-way cock valve, such as shown in FIG. 5 has heretofore been used for checking of blood pressure and injection of contrast media. An enlarged illustration of this triple three-way cock valve is shown in FIG. 6. First, a physiological saline solution is introduced into a syringe by the suction of a syringe while the cocks are operated to allow the suction. Then, the introduced physiological saline solution is pushed out of the syringe to fill the solution up to the front end of a catheter. The three cocks are operated to close a line of physiological saline solution; a line connecting to a pressure monitor is opened; and the catheter is inserted with the blood pressure of patient being monitored. When a contrast media is injected, the line connecting to a pressure monitor is closed (the line of physiological saline solution is also closed), the contrast media is filled in the syringe in a required amount by the suction of the syringe, and then the piston of the syringe is pushed to inject the contrast media from the front end of the catheter into the target site of vessel. Since the contrast media is a viscous liquid, a considerable pressure is needed for injection of the contrast media. An injection apparatus capable of conducting syringe operation mechanically has recently been developed, whereby use of a finer catheter has become possible. Nevertheless, the pressure required for injection has become as high as, for example, about 1,000 psi. Meanwhile, as the pressure monitor used for measurement of blood pressure, a small pressure transducer resistant to a pressure of about 400 mmHg is generally used; therefore, it ruptures easily when a high pressure is applied thereto. Hence, the above-mentioned switching of cocks has been requisite.

The switching of the triple three-way cock valve has been conducted manually, which has necessitated the presence of an operator and a patient in the same radiation room and has posed, to the operator, a problem of exposure to radiation. Further, an error in timing of the switching of cocks has led to the breakage of the pressure transducer. Particularly in Coronary artery having many branches, imaging is conducted for each branch by moving the catheter and, therefore, injection of contrast media is generally repeated about 10 times. During this period, the catheter inside is flushed with a physiological saline solution to prevent the coagulation of blood inside the catheter or the like. To conduct the injection and cutoff of contrast media, the flushing with physiological saline solution, etc. a plurality of times in correct timings has needed care and labor.

SUMMARY OF THE INVENTION

The present invention has been made in view of the above-mentioned problems of the prior art and the objective thereof is to provide a contrast media injection apparatus capable of conducting the monitoring of blood pressure and the injection of contrast media under no radiation exposure. The present invention also aims at providing a contrast media injection apparatus capable of conducting the injection of contrast media simply without requiring the complex operation of cock switching.

The present invention is directed to a contrast media injection apparatus comprising:

a manifold having a port for connection of catheter, a port for connection of contrast media line, a port for connection of pressure-monitoring line and a port for connection of physiological saline solution line, a pressure-monitoring line connected to the port for connection of pressure-monitoring line and having a cutoff mechanism in the middle, a contrast media line connected to the port for connection of contrast media line, and a contrast media injector connected to the back end of the contrast media line.

The contrast media injector is preferably an injector having a T-shaped one-way valve, a syringe and a syringe piston driving mechanism.

The cutoff means is preferably a two-way cock and preferably has a means for rotating the two-way cock.

In the present invention, it is preferred that the two-way cock is in an open state so as to enable monitoring of blood pressure, when no injection of contrast media is made and that the syringe piston driving mechanism and the means for rotating the two-way cock are driven synchronously so that the two-way cock is placed in a closed state before the piston of the syringe is moved forward and the injection of contrast media is started.

Another aspect of the present invention is further directed to a manifold having a port for connection of catheter, a port for connection of contrast media line, a port for connection of pressure-monitoring line and a port for connection of physiological saline solution line. This manifold is preferably used in the above-mentioned contrast media injection apparatus.

BRIEF DESCRIPTION OF THE DRAWINGS

FIG. 6 is a drawing showing the triple three-way cock valve, used in a conventional contrast media injection apparatus or in manual injection of contrast media.

DETAILED DESCRIPTION OF THE INVENTION

Figure 1:
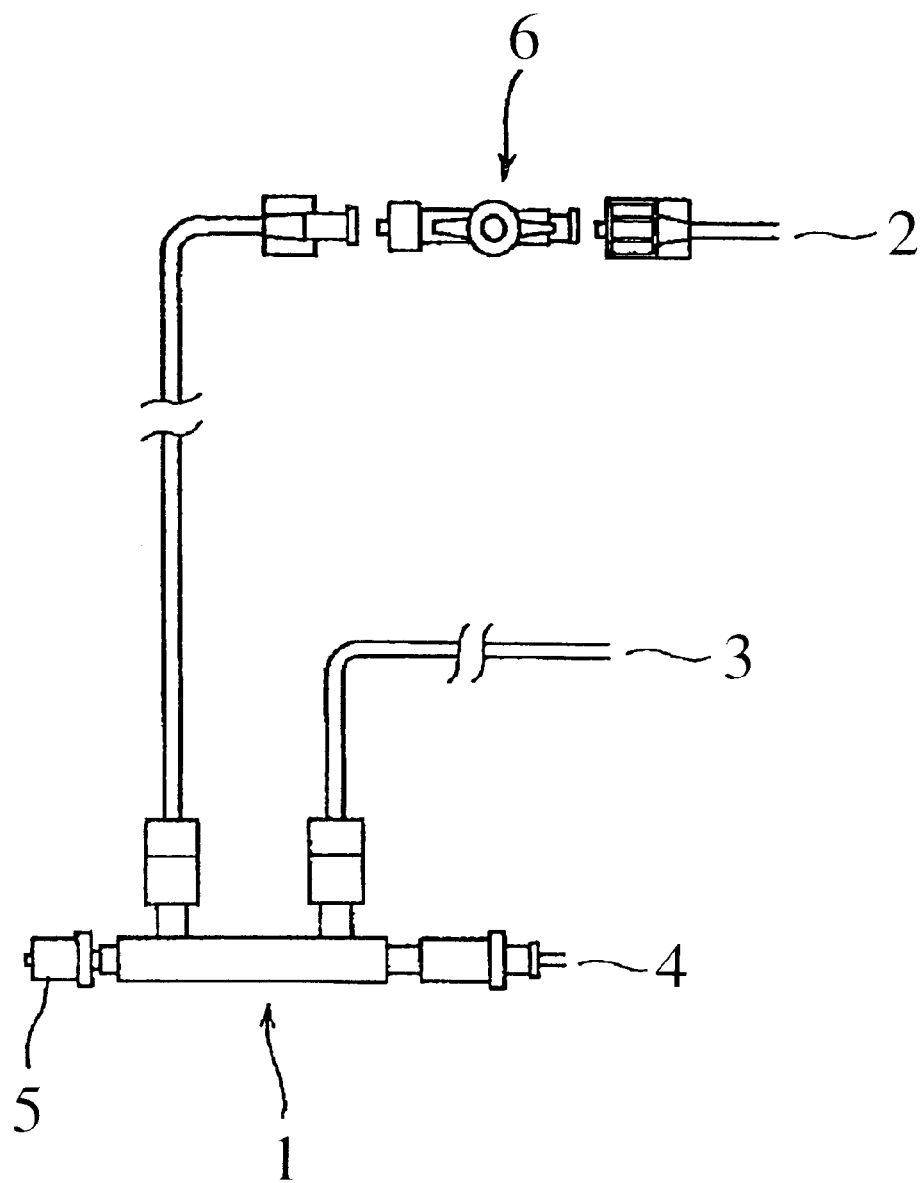
FIG. 1 is a drawing showing the total picture of an example of the contrast media injection apparatus of the present invention.
Figure 2:
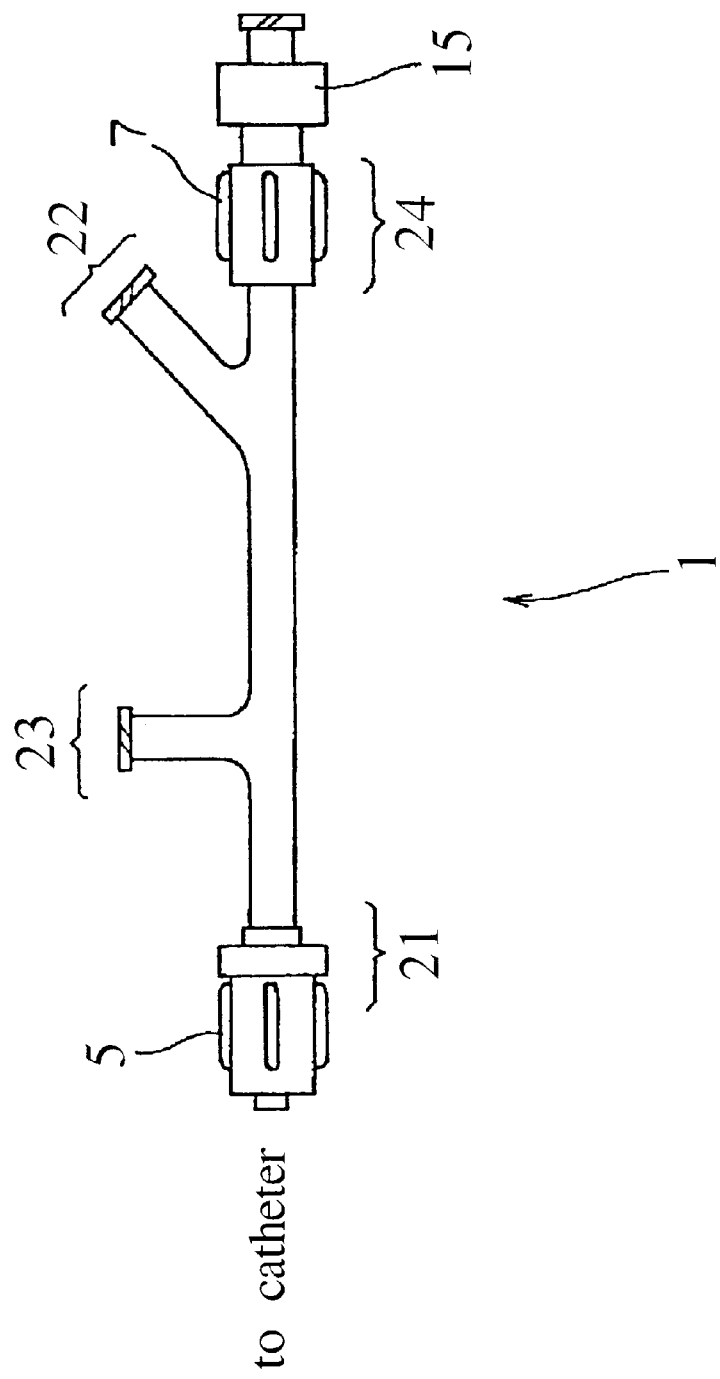
FIG. 2 is a drawing showing an example of the manifold used in the contrast media injection apparatus of the present invention.

In FIG. 1 is shown a drawing of the total picture of an example of the contrast media injection apparatus of the present invention; and in FIG. 2 is shown an enlarged drawing of an example of the manifold used in the contrast media injection apparatus of the present invention. A manifold 1 has a port 21 for connection of catheter, a port 22 for connection of contrast media line, a port 23 for connection of pressure-monitoring line, and a port 24 for connection of physiological saline solution line. In the present invention, each port of manifold means the front end of each manifold branch to which a catheter or a line (generally a tube) is fitted. In FIG. 2, the port 21 for connection of catheter and the port 24 for connection of physiological saline solution line are shown in a state that connectors 5 and 7 are fitted to the port 21 and the port 24, respectively, and no branch end is shown for these ports.

To the ports 21, 22, 23 and 24 are connected a catheter, a contrast media line 3, a pressure-monitoring line 2 and a physiological saline solution line 4, respectively. The catheter is connected to the catheter connection port 21 directly or via an extension tube or the like. With respect to the shape of the manifold in the examples shown in FIG. 1 and FIG. 2, the length is about 5 to 20 cm (specifically about 8 to 15 cm) and the tube diameter is about 3 to 15 mm (specifically about 4 to 10 mm); and each port has a flange having a diameter larger than the tube diameter by about 1 to 2 mm in order to make easy the fitting of a corresponding line or the like and further avoid the slipping of the line or the like off the port. Thus, the shape of the manifold used in the present invention is not particularly restricted to the shape shown in FIG. 1 and FIG. 2 as long as the manifold has one outlet port as catheter connection port and at least three inlet ports and each line or the like is connectable thereto. The material for the manifold is preferably a plastic such as polycarbonate, polypropylene or the like.

The pressure-monitoring line 2 has a cutoff mechanism in the middle and, when in an open state, transmits the blood pressure to a pressure monitor connected to the opposite end of the line, via a physiological saline solution or contrast media filled in the tube constituting the line. When the line is closed by the action of the cutoff mechanism, there is no continuity of the tube-inside liquid between the two sides of the cutoff mechanism and, therefore, the pressure or pressure change at the manifold side is not transmitted to the pressure monitor.

As such a cutoff mechanism, a simple two-way cock 6 shown in FIG. 1 can be used.

In the present invention, the cutoff mechanism is preferably remote-controllable by an electrical means; when the cutoff mechanism is a two-way cock, it preferably has a means (e.g. motor) capable of rotating the two-way cock for its opening or closing. When the motor is remote-controllable, the opening or closing of the two-way cock can be conducted under no radiation exposure.

Figure 3:
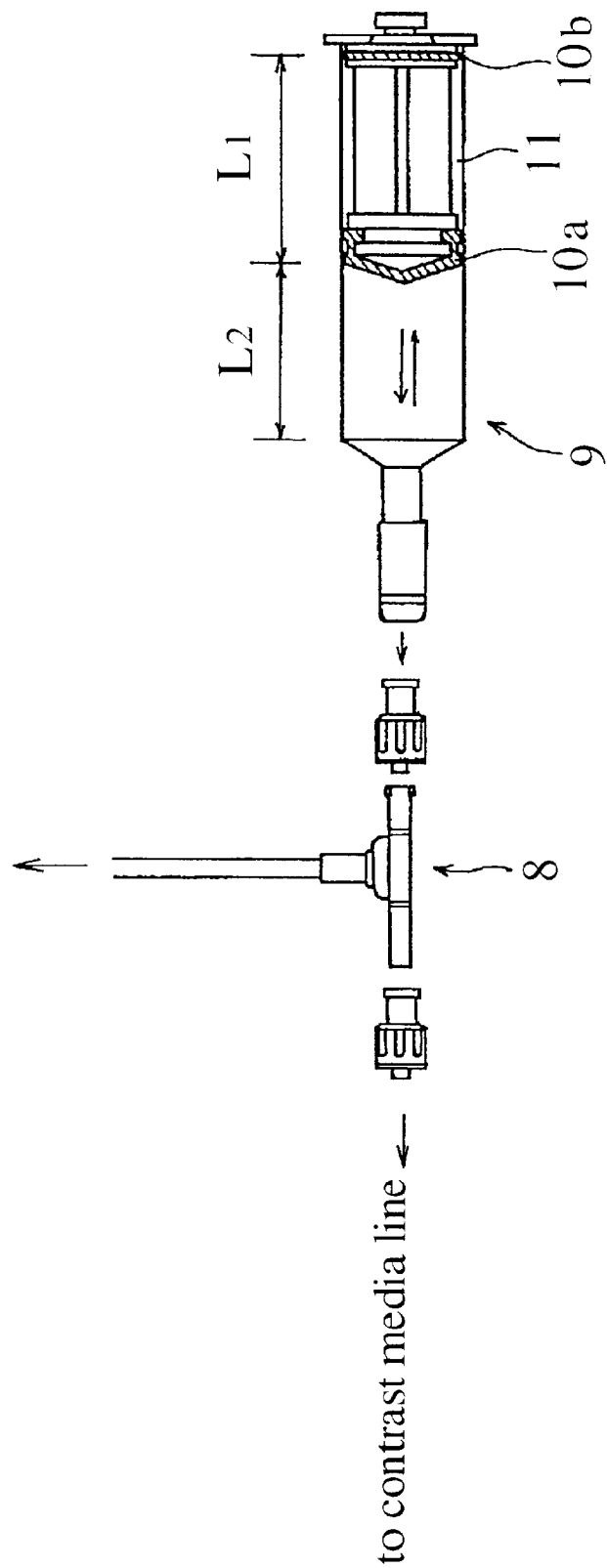
FIG. 3 is a drawing showing an example of the contrast media injector used in the contrast media injector apparatus of the present invention.

To the back end of the contrast media line 3 is fitted, for example, a contrast media injector. The contrast media injector has valves (or parts having a valve action); when injection of contrast media is made, a contrast media is sent from the contrast media line 3 to the manifold 1 by the contrast media injector and, when no injection is made, the contrast media injector is cut off. An example of the contrast media injector is shown in FIG. 3. This contrast media injector is constituted by a T-shaped one-way valve 8 and a syringe 9. When the piston of the syringe is moved backward, a negative pressure is generated, whereby the valve at the contrast media container side is opened (the valve at the contrast media line side is closed) and a contrast media is introduced into the syringe. When the piston is moved forward, a positive pressure is generated, whereby the valve at the contrast media container side is closed (the valve at the contrast media line side is opened) and the contrast media is sent out.

In the present invention, it is preferred to use a means for moving the syringe piston. As such a means, there is preferably used, for example, a device having a syringe holder for holding the syringe, a piston holder for holding the piston, and a motor capable of moving the piston holder and the piston forward and backward. When the piston is moved backward, a contrast media is sucked into the syringe and, when the piston is moved forward, the sucked contrast media is sent out. This device can control the actions of piston such as the distance of forward or backward movement based on the set value of to-be-injected volume, the speed of movement, the timing of injection, and the like, and further has a switch for start or stop of piston movement, etc.

As to the kind of the syringe used in the contrast media injector, there is no particular restriction; however, a syringe of double-packing structure shown in FIG. 3, having two packings at the front end and back end of the piston is preferred. In the syringe of FIG. 3, a packing 10a is fitted to the front end of the piston and a packing 10b is fitted to the back end of the piston; and the distance $L_2$ of forward or backward movement of the piston is set so as to be the same as or smaller than the distance $L_1$ between the packings 10a and 10b. In this setting, the inner wall of the syringe which comes in contact with the contrast media when the piston is moved most backward (a state of FIG. 3), makes no direct contact with the outside atmosphere even when the syringe is moved most forward, and is in the space between the packings 10a and 10b, i.e. a clean space 11. Therefore, even when the piston repeats a reciprocating motion, the contrast media is injected under no contact with the outside air and the contrast media does not become filthy and can retain a sterile state.

The syringe of double-packing structure can retain a highly sterile state also when used in a contrast media injection apparatus of conventional type or in a syringe pump used for manual injection of contrast media.

In the present invention, the action of the syringe piston of the contrast media injector and the action of the two-way cock 6 provided in the middle of the pressure-monitoring line may be controlled by respective switches or signals. No radiation exposure takes place as long as the above actions are controlled remotely. However, when the ON/OFF timing of switch is mistaken and the syringe piston is moved forward in a state that the two-way cock provided in the middle of the pressure-monitoring line leading to a pressure transducer is opened, a high pressure is applied to the pressure transducer, resulting in breakage of the pressure transducer. Hence, in the present invention, it is preferred that the action of the syringe piston of the contrast media injector and the action of the two-way cock provided in the middle of the pressure-monitoring line are allowed to take place sequentially. That is, when a sign of start of contrast media injection (switch ON) is issued to the syringe piston driving mechanism, first the two-way cock is put in an OFF state and then the syringe piston is allowed to move forward; thereby, no breakage of the pressure transducer takes place. In general, a certain time takes from the start of rotation of the two-way cock to the complete OFF state. Therefore, in view of the time taken from the issuance of the signal for rotating the two-way cock, to the complete OFF state, a signal is issued so that the syringe piston is allowed to move forward after a certain delay time (for example, about 0.5 second), whereby the breakage of the pressure transducer can be prevented.

Figure 4:
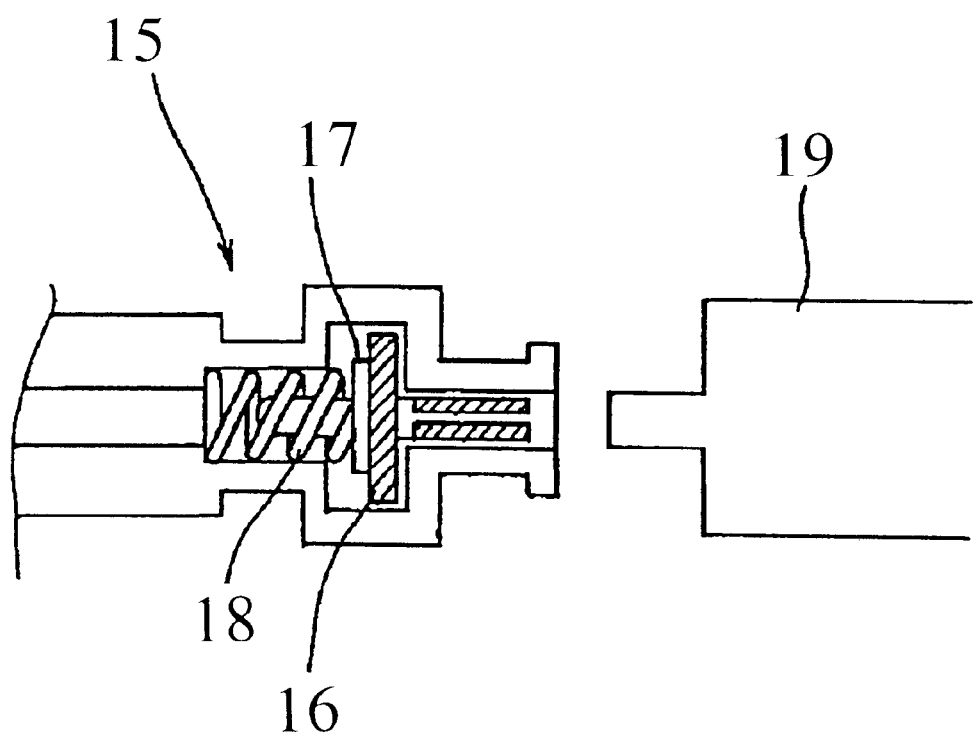
FIG. 4 is a drawing of an example of the valve-containing connector used in the physiological saline solution line connected to the contrast media injection apparatus of the present invention.
Figure 5:
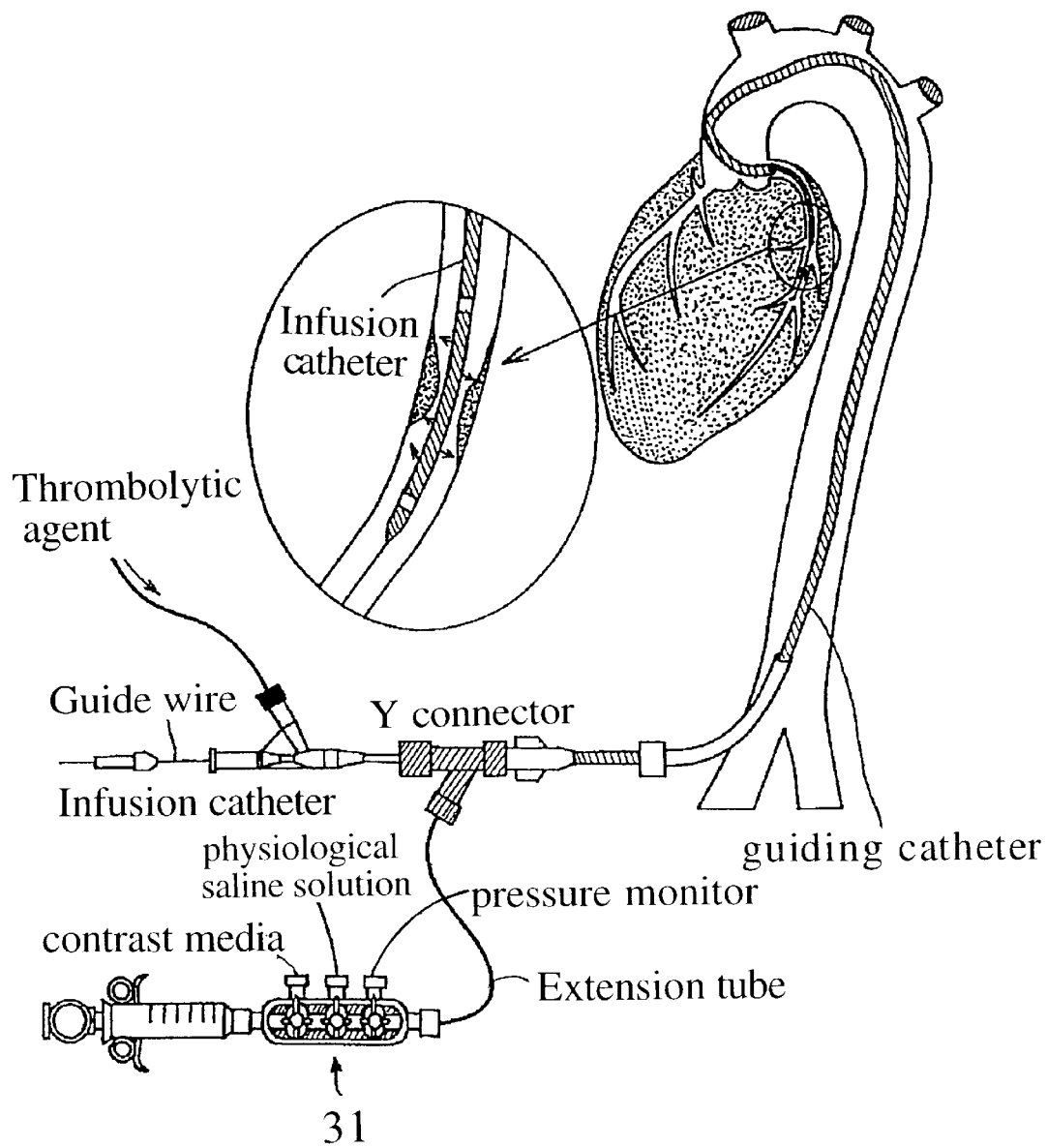
FIG. 5 is a drawing showing a conventional method for injection of contrast media.

In the present invention, the physiological saline solution line 4 can be any line as long as a physiological saline solution is allowed to flow through the line in one way. For example, a physiological saline solution may be allowed to flow by a pump using a piston driving mechanism and a syringe both similar to those mentioned above for injection of contrast media. However, since a physiological saline solution is generally used only for filling the insides of catheter, pressure-monitoring line, contrast media line, etc. and further for preventing blood from coagulation, the mechanism for sending a physiological saline solution may be, for example, a valve-containing connector 15 such as shown in FIG. 4, which is operated simply. In FIG. 2, a valve-containing connector 15 is fitted to the manifold of the present invention. When a syringe 19 (for physiological saline solution) is fitted to this valve-containing connector, the front end of the syringe pushes and opens the valve seat 16 of the connector 15; a physiological saline solution is sent out from the syringe 19, and the insides of catheter, pressure-monitoring line, contrast media line, etc. are filled with the physiological saline solution; then, when the syringe 19 is removed, the spring 18 of the connector 15 pushes the valve seat 16 via the valve pad 17 to cut off the flow path at the syringe side.

The above-explained contrast media injection apparatus of the present invention is preferably used in angiography. It is used as follows, for example. To each port of the manifold are connected a catheter, a contrast media line, a pressure-monitoring line and a physiological saline solution line by flushing the physiological saline solution; then, a physiological saline solution is filled in the system; thereafter, the physiological saline solution line is closed and the two-way cock (cutoff mechanism) of the pressure-monitoring line is opened; in this state, the catheter is inserted into a patient to the vessel site to which a contrast media is to be inserted; then, injection of the contrast media is started. By synchronizing, as mentioned previously, the timing of rotation of the two-way cock provided in the middle of the pressure-monitoring line, with the timing of injection of the contrast media, the two-way cock is closed right before the start of contrast media injection, whereby the breakage of the pressure transducer can be prevented effectively. Further, by allowing the two-way cock to reopen when the injection of contrast media is stopped, continued measurement of blood pressure is made possible even after the completion or intermission of injection of contrast media. Therefore, when a large number of branch vessels of, for example, coronary artery are imaged successively, measurement of blood pressure is possible during the transfer of catheter from one branch to next branch.

According to the present invention, there can be provided a contrast media injection apparatus capable of conducting the monitoring of blood pressure and the injection of contrast media under no radiation exposure. According to another aspect of the present invention, there can be provided a contrast media injection apparatus capable of conducting the injection of contrast media simply without requiring the complex operation of cock switching.

What is claimed is:

1. A contrast media injection apparatus comprising:
   (a) a manifold having a port for connection of catheter, a port for connection of contrast media line, a port for connection of pressure-monitoring line and a port for connection of physiological saline solution line,
   (b) a pressure-monitoring line connected to the port for connection of pressure-monitoring line and having a cutoff mechanism in the middle of the pressure-monitoring line connecting a pressure monitor with the port for connection of pressure-monitoring line,
   (c) a contrast media line connected to the port for connection of contrast media line, and
   (d) a contrast media injector connected to the back end of the contrast media line.

2. A contrast media injection apparatus according to claim 1, wherein the contrast media injector has a T-shaped one-way valve, a syringe and a syringe piston driving mechanism.

3. A contrast media injection apparatus according to claim 2, wherein the syringe has a double-packing structure wherein each one packing is provided at the front end of the piston and at the back end of the piston and wherein the distance of forward or backward piston movement is set so as to be the same as or smaller than the distance between the two packings.

4. A contrast media injection apparatus according to claim 1, wherein the cutoff mechanism is a two-way cock and has a rotating mechanism of the two-way cock.

5. A contrast media injection apparatus according to claim 1, wherein
   the contrast media injector has a T-shaped one-way valve, a syringe and a syringe piston driving mechanism,
   the cutoff mechanism is a two-way cock and has a rotating mechanism of the two-way cock,
   when no injection of contrast media is made, the two-way cock is in an open state and enables monitoring of blood pressure, and
   the syringe piston driving mechanism and the rotating mechanism of the two-way cock are driven synchronously so that the two-way cock is placed in a closed state before the piston of the syringe is moved forward and the injection of contrast media is started.

6. A contrast media injection apparatus according to claim 5, wherein the port for connection of physiological saline solution is connected with a valve-containing connector whose valve is opened when a syringe for physiological saline solution is connected to the connector and is closed when the syringe is removed.

7. A contrast media injection apparatus according to claim 1, wherein the port for connection of physiological saline solution is connected with a valve-containing connector whose valve is opened when a syringe for physiological saline solution is connected to the connector and is closed when the syringe is removed.

8. A contrast media injection apparatus according to claim 5, wherein the syringe has a double-packing structure wherein each one packing is provided at the front end of the piston and at the back end of the piston and wherein the distance of forward or backward piston movement is set so as to be the same as or smaller than the distance between the two packings.

9. A contrast media injection apparatus used in angiography comprising:
- a manifold comprising port A for connecting a catheter, port B for connecting a contrast media line, port C for connecting a pressure-monitoring line, and port D for connecting a physiological saline solution line, all of which ports are interconnected inside the manifold without cock valves;
- a pressure-monitoring line connected to port C, said pressure-monitoring line being provided with a cutoff device disposed in the middle of the pressure-monitoring line connecting a pressure monitor with port C;
- a contrast media line connected to port B; and
- a contrast media injector connected to a distal end of the contrast media line.

10. A contrast media injection apparatus comprising:
- (a) a manifold having a port for connection of catheter, a port for connection of contrast media line, a port for connection of pressure-monitoring line and a port for connection of physiological saline solution line,
- (b) a pressure-monitoring line connected to the port for connection of pressure-monitoring line, said pressure-monitoring line having a cutoff mechanism, said cutoff mechanism being a two-way cock and having a rotating mechanism of the two-way cock, wherein when no injection of contrast media is made, the two-way cock is in an open state and enables monitoring of blood pressure,
- (c) a contrast media line connected to the port for connection of contrast media line, and
- (d) a contrast media injector connected to the back end of the contrast media line, said contrast media injection having a T-shaped one-way valve, a syringe and a syringe piston driving mechanism, said syringe piston driving mechanism and said rotating mechanism of the two-way cock being driven synchronously to place the two-way cock in a closed state before the piston of the syringe moves forward and the injection of contrast media starts.

11. A contrast media injection apparatus comprising:
- (a) a manifold having a port for connection of catheter, a port for connection of contrast media line, a port for connection of pressure-monitoring line and a port for connection of physiological saline solution line,
- (b) a pressure-monitoring line connected to the port for connection of pressure-monitoring line, said pressure-monitoring line having a cutoff mechanism,
- (c) a contrast media line connected to the port for connection of contrast media line, and
- (d) a contrast media injector connected to the back end of the contrast media line, said contrast media injector having a T-shaped one-way valve, a syringe, and a syringe piston-driving mechanism, said syringe having a double-packing structure wherein each one packing is provided at the front end of the piston and at the back end of the piston and wherein the distance of forward or backward piston movement is set so as to be the same as or smaller than the distance between the two packings.

12. A contrast media injection apparatus comprising:
- (a) a manifold having a port for connection of catheter, a port for connection of contrast media line, a port for connection of pressure-monitoring line and a port for connection of physiological saline solution line,
- (b) a pressure-monitoring line connected to the port for connection of pressure-monitoring line and having a cutoff mechanism in the middle of the pressure-monitoring line,
- (c) a contrast media line connected to the port for connection of contrast media line, and
- (d) a contrast media injector connected to the back end of the contrast media line,
- wherein the contrast media injector has a T-shaped one-way valve, a syringe and a syringe piston driving mechanism.

13. A contrast media injection apparatus comprising:
- (a) a manifold having a port for connection of catheter, a port for connection of contrast media line, a port for connection of pressure-monitoring line and a port for connection of physiological saline solution line,
- (b) a pressure-monitoring line connected to the port for connection of pressure-monitoring line and having a cutoff mechanism in the middle of the pressure-monitoring line,
- (c) a contrast media line connected to the port for connection of contrast media line, and
- (d) a contrast media injector connected to the back end of the contrast media line,
- wherein the port for connection of physiological saline solution is connected with a valve-containing connector whose valve is opened when a syringe for physiological saline solution is connected to the connector and is closed when the syringe is removed.

* * * * *